United States Patent [19]

Ueno et al.

[11] Patent Number: 4,785,122

[45] Date of Patent: Nov. 15, 1988

[54] METHOD FOR PRODUCTION OF AMINE COMPOUND

[75] Inventors: Tsunemasa Ueno, Kawasaki; Yutaka Morimoto, Yokohama, both of Japan

[73] Assignee: Nippon Shokubai Kagaku Kogyo Co. Ltd., Osaka, Japan

[21] Appl. No.: 119,055

[22] Filed: Nov. 10, 1987

[30] Foreign Application Priority Data

Nov. 11, 1986 [JP] Japan ................................ 61-266588

[51] Int. Cl.[4] .......................................... C07D 307/52
[52] U.S. Cl. ................................................... 549/495
[58] Field of Search .......................................... 549/495

[56] References Cited

U.S. PATENT DOCUMENTS

| | | | |
|---|---|---|---|
| 4,128,658 | 12/1978 | Price et al. | 549/495 X |
| 4,169,855 | 10/1979 | Price et al. | 549/495 X |
| 4,255,440 | 3/1981 | Price et al. | 549/495 X |
| 4,279,819 | 7/1981 | Price et al. | 549/495 |
| 4,394,516 | 7/1983 | Clitherow | 549/495 |

*Primary Examiner*—Richard L. Raymond
*Attorney, Agent, or Firm*—Omri M. Behr

[57] ABSTRACT

A method for the producing 2-[[[5-(dialkylamino)alkyl-2-furanyl]methyl]thio]-ethane amine by the reaction of cysteamine or cysteamine hydrochloride containing free hydrogen chloride with 5-(dialkyl amino)alkyl furfuryl alcohol, which method can be obtained the product in a highly yield by carrying out said reaction at a temperature in the range of 30° to 80° C.

9 Claims, 2 Drawing Sheets

METHOD FOR PRODUCTION OF AMINE COMPOUND

BACKGROUND OF THE INVENTION

1. Field of the Invention:

This invention relates to a method for the production of amine compounds useful for manufacture of medicines. More particularly, it relates to an improved method for the production of an amine compound, which effects the production by the reaction of 5-(dialkylamino)alkyl furfuryl alcohol with an aqueous solution of cysteamine or cysteamine hydrochloride.

1. Description of the Prior Art:

The amine compounds according with the present invention are compounds useful as various intermediates for pharmaceuticals, e.g., as intemediates for ranitidine which is medicines represented by the formula III:

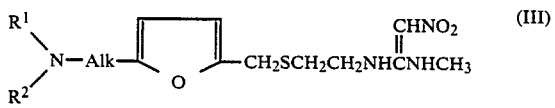

wherein $R^1$ and $R^2$ independently stand for an alkyl group of 1 to 4 carbon atoms and Alk stands for an alkylene chain of 1 to 4 carbon atoms.

The amine compounds represented by the formula II:

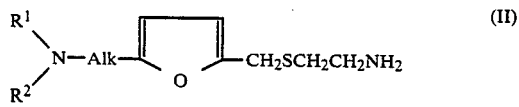

wherein $R^1$ and $R^2$ independently stand for an alkyl group of 1 to 4 carbon atoms and Alk stands for an alkylene chain of 1 to 4 carbon atoms, are said to be produced advantageously by a method resorting to the reaction of 5-(dialkylamino)alkyl furfuryl alcohols represented by the formula I:

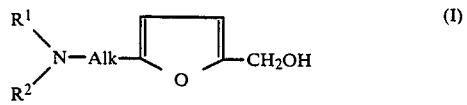

wherein $R^1$, $R^2$, and Alk have the same meanings as defined above (or acylation products thereof) (U.S. Pat. Nos. 4,128,658; 4,169,855; 4,255,440; and 4,279,819).

This method, however, has the disadvantage that the reaction calls for a long time, the yield is low, and the productivity is poor. The method of the U.S. patent requires the reaction to be carried out in concentrated hydrochloric acid at a temperature of 0° C. In the reaction performed for 22 hours, the conversion of a 5-(dialkylamino)alkyl furfuryl alcohol is 80% and the yield is as low as 55%.

An object of this invention, therefore, is to provide a novel method for the production of amine compounds.

Another object of this invention is to provide a method for producing commercially advantageously a [5-(dialkylamino)alkyl-2-furanyl]-methyl]thio]ethane amine of high purity in a high yield.

SUMMARY OF THE INVENTION

The objects described above are accomplished by a method for the production of a 2-[[[5-(dialkylamino)alkyl-2-furanyl]methyl]-thio]ethane amine represented by the formula II:

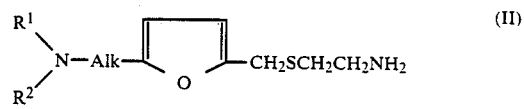

wherein $R^1$ and $R^2$ independently stand for an alkyl group of 1 to 4 carbon atoms and Alk stands for an alkylene chain of 1 to 4 carbon atoms, by the reaction of a 5-(dialkylamino)alkylfurfuryl alcohol represented by the formula I:

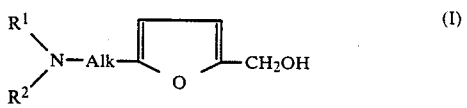

wherein $R^1$, $R^2$, and Alk have the same meanings as defined above, with cysteamine or cysteamine hydrochloride in the presence of free hydrogen chloride at a temperature in the range of 30° to 80° C.

DESCRIPTION OF PREFERRED EMBODIMENT

Figure 1:
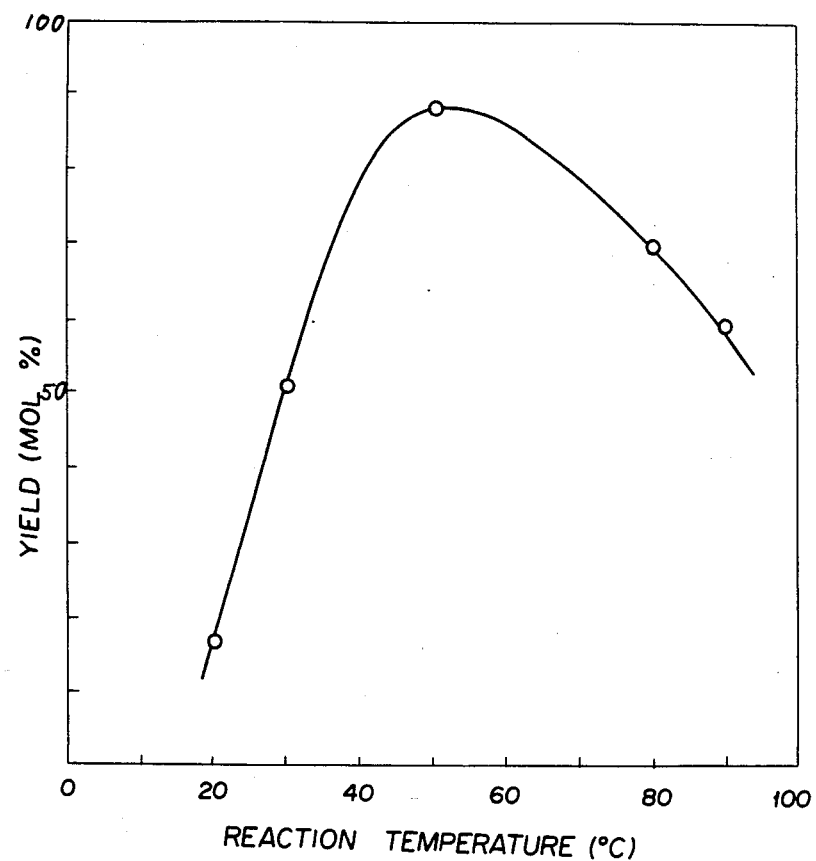
FIG. 1 is a graph showing the relation between reaction temperature and yield.

The reaction of a 5-(dialkylamino)alkylfurfuryl alcohol with cysteamine or hydrochloride thereof is desirably carried out by a process which comprises mixing hydrochloric acid with cysteamine or hydrochloride thereof thereby preparing an aqueous solution of cysteamine hydrochloride containing free hydrogen chloride and causing this aqueous cysteamine hydrochloride solution to react with a 5-(dialkylamino)alkylfurfuryl alcohol represented by the aforementioned formula I at a temperature in the range of 30° to 80° C., more desirably 40° to 70° C., and most desirably 45° to 55° C., for a period in the range of 15 minutes to 3 hours, more desirably 20 to 150 minutes, and most desirably 30 to 120 minutes. Under these conditions, the reaction is completed to give the compound in a yield in the range of 80 to 90 mol%. The reaction proceeds very slowly and the yield and selectivity of the reaction are both inferior and the productivity is poor if the temperature is less than 30° C. If the reaction temperature exceeds 80° C., the disadvantage arises that the reaction product lacks stability and, consequently, the reaction of decomposition tends to predominate so much as to impair the yield and the selectivity.

The free hydrogen chloride must be used in an amount of not less than 1 mols, preferably not less than 2 mols, per mol of the raw material, 5-(dialkylamino)alkylfurfuryl alcohol represented by the formula I. From the standpoint of economy and productivity, the amount of the hydrogen hydrochloride is desired to be not more than 5 mols, preferably not more than 4 mols, per mol of the raw material. The concentration of the free hydrogen chloride in the aqueous cysteamine hydrochloride solution is desired to be not less than 5% by weight, preferably 7 to 30% by weight, the most preferably 8 to 25% by weight.

The cysteamine (2-aminoethane thiol) or the hydrochlordie thereof is used in an amount in the range of 0.5 to 3 mols, more desirably 0.8 to 1.5 mols, and most desirably 1 to 1.2 mols, per mol of the 5-(dialkylamino)alkylfurfuryl alcohol represented by the formula I. It may be used in the form of powder or aqueous solution. From the operational point of view, it is desired to be used in the form of aqueous solution. In the formula I representing the 5-(dialkylamino)alkylfurfuryl alcohol, i.e. the starting material for the method of this invention, $R^1$ and $R^2$ independently stand for an alkyl group of 1 to 4 carbon atoms, more desirably 1 or 2 carbon atoms, and most desirably methyl group and Alk stands for an alkylene group of 1 to 4 carbon atoms, more desirably 1 or 2 carbon atoms, and most desirably methylene group.

Especially when the aqueous cysteamine hydrochloride solution is used, the process can be operated continuously and productivity increases remarkably.

Figure 2:
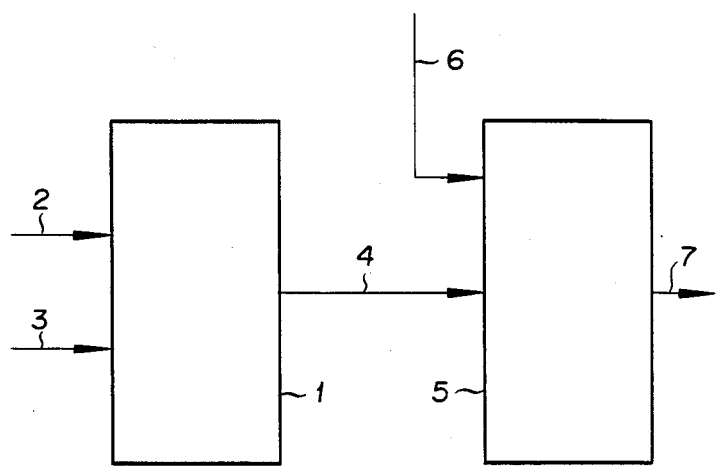
FIG. 2 is a flow diagram of an embodiment of the present invention.

The continuous process is explained in detail referring FIG. 2. In a device shown in FIG. 2, hydrochloric acid is fed through a conduit 2 to a reactor 1 maintained at a temperature of 0° to 80° C., preferably 10° to 60° C., most preferably 10° to 40° C. 5-(Dialkylamino)alkylfurfuryl alcohol is fed through a conduit 3 to the reactor 1. A hydrochloric acid solution of 5-(dialkylamino)alkylfurfuryl alcohol hydrochloride thus formed is continuously fed to a reactor 5 through a conduit 4. Under maintaining a temperature of the reactor 5 at 30° to 80° C., preferably 40° C. to 70° C., an aqueous cysteamine hydrochloride solution is fed to the reactor 5 through a conduit 6, and a reaction product is continuously discharged from a conduit 7.

Now, the present invention will be described more specifically below with reference to working examples thereof.

EXAMPLE 1

In a mixture containing 38.5 g of an aqueous 36 wt% hydrochloric acid solution and 13.3 g of an aqueous 75 wt% cysteamine hydrochloride solution, 13.0 g of 5-(dimethylamino)methylfurfuryl alcohol was added dropwise and left reacting therein at 50° C. for 30 minutes. By gas chromatography, the yield of reaction of 2-[[[5-dimetylamino)methyl-2-furanyl]-methyl]thio]-ethane amine was found to be 89 mol% relative to 5-(dimethylamino)methylfurfuryl alcohol and the selectivity of the reaction to be 89 mol%. From the resultant reaction mixture in the presence of anhydrous sodium chloride added thereto in an excess amount, the product of the reaction was extracted with diethyl ether. The crude product was distilled under a vacuum to expel the solvent and isolate 14.3 g of 2-[[[5-(dimethylamino)-methyl-2-furanyl]methyl]thio]-ethane amine (boiling at 134° C./1 mmHg).

EXAMPLE 2

In a mixture containing 45.9 g of an aqueous 30 wt% hydrochloric acid solution and 10.0 g of cysteamine hydrochloride, 3.0 g of 5-(dimethylamino)methylfurfuryl alcohol was added dropwise and left reacting at 50° C. for 30 minutes. By gas chromatography, the reaction yield of 2-[[[5-(dimethylamino)methyl-2-furanyl]methyl]thio]-ethane amine was found to be 87 mol% relative to 5-(dimethylamino)methylfurfuryl alcohol and the selectivity of the reaction to be 87 mol%. From the resultant reaction mixture and in the presence of anhydrous sodium carbonate added thereto in an excess amount, the product of the reaction was extracted with diethyl ether. The crude product was distilled under a vacuum to expel the solvent and isolate 13.9 g of 2-[[[5-(dimethylamino)methyl-2-furanyl]methyl]thio]-ethane amine (boiling at 134° C./1 mmHg).

EXAMPLE 3

In a mixture containing 51.8 g of an aqueous 27 wt% hydrochloric acid solution and 13.3 g of an aqueous 75 wt% cysteamine hydrochloride solution, 13.0 g of 5-(dimethylamino)methylfurfuryl alcohol was added dropwise and left reaction at 50° C. for 30 minutes. By gas chromatography, the reaction yield of 2-[[[5-(dimethylamino)methyl-2-furanyl]methyl]thio]-ethane amine was found to be 74 mol% relative to 5-(dimethylamino)methylfurfuryl alcohol and the selectivity of the reaction to be 88 mol%. When the reaction was further continued for 1.5 hours for perfection of the reaction, the reaction yield was found to be 85 mol% and the selectivity of the reaction to be 85 mol% by the same analysis. From the resultant reaction mixture in the presence of anhydrous sodium carbonate added thereto in an excess amount, the product of the reaction was extracted with diethyl ether. The crude product was distilled under a vacuum to expel the solvent and isolate 13.0 g of 2-[[[5-(dimethylamino)methyl-2-furanyl]methyl]thio]-ethane amine (boiling at 134° C./1 mmHg).

Control 1

In a mixture containing 38.5 g fo an aqueous 36 wt% hydrochloric acid solution and 10.0 g of cysteamine hydrochloride, 13.0 g of 5-(dimethylamino)methylfurfuryl alcohol was added dropwise and left standing at 0° C. for 22 hours. By gas chromatography, the reaction yield of 2-[[[5-(dimethylamino)methyl-2-furanyl]methyl]thio]-ethane amine was found to be 55 mol% relative to 5-(dimethylamino)methylfurfuryl alcohol and the selectivity of the reaction to be 68 mol%.

Control 2

In a mixture containing of 38.5 g of an aqueous 36 wt% hydrochloric acid solution and 13.3 g of an aqueous 75 wt% cysteamine hydrochlroride solution, 13.0 g of 5-(dimethylamino)methylfrufryl alcohol was added dropwise and left reacting at 20° C. for 30 minutes. By gas chromatography, the reaction yield of 2-[[[5-dimethylamino)methyl-2-furanyl]methyl]thio]-ethane amine was found to be 17 mol% relative to 5-(dimethylamino)-methylfurfuryl alcohol and the selectivity of the reaction was 72 mol%.

These two control experiments indicate that the reactions performed at low temperatures proceeded very slowly and the selectivities of reaction were poor.

Control 3

In a mixture containing 38.5 g of an aqueous 36 wt% hydrochloric acid solution and 13.3 g of an aqueous 75 wt% cysteamine hydrochloride solution, 13.0 g of 5-(dimethylamino)methylfurfuryl alcohol was added dropwise and left reacting at 90° C. for 30 minutes. By gas chromatogrphy, the reaction yield of 2-[[[5-(dimethylamino)methyl-2-furanyl]methyl]thio]-ethane amine was found to be 60 mol% relative to 5-(dimethylamino)-methylfurfuryl alcohol and the selectivity of the reaction to be 60 mol%.

This control experiment indicates that the reaction performed at a high temperature gave poor yield and poor selectivity of the reaction.

EXAMPLE 4

In a mixture containing 47.2 g of an aqueous 36 wt% hydrochloric acid solution and 9.0 g of an aqueous 75 wt% systeamine solution, 13.0 g of 5-(dimethylamino)-methylfurfuryl alcohol was added dropwise and left reacting at 50° C. for 30 minutes. By gas chromatography, the reaction yield of 2-[[[5-(dimethylamino)methyl-2-furanyl]methyl]thio]-ethane amine was found to be 87 mol% and the selectivity of the reaction to be 87 mol%. From the resultant reaction mixture in the presence of anhydrous sodium carbonate added thereto in an excess amount, the product of the reaction was extracted with diethyl ether. The crude product was distilled under a vacuum to expel the solvent and isolate 13.0 g of 2-[[[5-(dimethylamino)methyl-2-furanyl]methyl]thio]-ethane amine (boiling at 134° C./1 mmHg).

EXAMPLE 5

In a mixture containing 56.6 g of an aqueous 30 wt% hydrochloric acid solution and 6.5 g of cysteamine, 13.0 g of 5-(dimethylamino)methylfurfuryl alcohol was added dropwise and left reacting at 50° C. for 30 minutes. By gas chromatography, the reaction yield of 2-[[[5-(dimethylamino)methyl-2-furanyl]methyl]thio]-ethane amine was found to be 68 mol% and the selectivity of the reaction was to be 86 mol%. When the reaction was further continued for 1.5 hours and analyzed by the same method, the reaction yield was found to be 85 mol% and the selectivity of the reaction to be 85 mol%.

Then, from the resultant reaction mixture in the presence of anhydrous sodium carbonate added thereto in an excess amount, the product of the reaction was extracted with diethyl ether. The crude product was distilled under a vacuum to expel the solvent and isolate 12.7 g of 2-[[[5-(dimethylamino)methyl-2-furanyl]methyl]thio]-ethane amine (boiling at 134° C./1 mmHg).

Control 4

In a mixture containing 47.2 g of an aqueous 36 wt% hydrochloric acid solution and 6.3 g of cysteamine, 13.0 g of 5-(dimethylamino)methylfurfuryl alcohol was added dropwise and left standing at 0° C. for 22 hours. By gas chromatography, the reaction yield of 2-[[[5-(dimethylamino)methyl-2-furanyl]methyl]thio]-ethane amine was found to be 60 mol% relative to 5-(dimethylamino)methylfurfuryl alcohol and the selectivity of the reaction to be 66 mol%.

EXAMPLE 6

In a mixture containing 38.5 g of an aqueous 36 wt% hydrochloric acid solution and 13.3 g of an aqueous 75 wt% cysteamine hydrochloride solution, 13.0 g of 5-(dimethylamino)methylfurfuryl alcohol was added dropwise and left reacting at 30° C. for 30 minutes. By gas chromatography, the reaction yield of 2-[[[5-(dimethylamino)methyl-2-furanyl]methyl]thio]-ethane amine was found to be 51 mol% relative to 5-(diaminomethyl)-methylfurfuryl alcohol and the selectivity of the reaction to be 73 mol%. When the reaction was further continued for 1.5 hours and then analyzed by the same method, the reaction yield was found to be 74 mol% and the selectivity of the reaction to be 77 mol%.

EXAMPLE 7

In a mixture containing 38.5 g of an aqueous 36 wt% hydrochloric acid solution and 13.3 g of an aqueous 75 wt% cysteamine hydrochloride solution, 13.0 g of 5-(dimethylamino)methylfurfuryl alcohol was added dropwise and left reacting at 80° C. for 30 minutes. By gas chromatography, the reaction yield of 2-[[[5-(dimethylamino)methyl-2-furanyl]methyl]thio]-ethane amine was found to be 70 mol% relative to 5-(diaminomethyl)-methylfurfuryl alcohol and the selectivity of the reaction to be 70 mol%. When the reaction was further continued for 1.5 hours and then analyzed by the same method, the reaction yield was found to be 50 mol% and the selectivity of the reaction to be 50 mol%.

When relations between reaction temperatures and yields obtained from Example 1, 6, and 7 and controls 2 and 3 were plotted, a graph indicated in a drawing was obtained.

EXAMPLE 8

In a device shown in FIG. 2, 38.5 kg/hr of aqueous 36 wt% hydrochloric acid solution was fed through a conduit 2 and 13.0 kg/hr of 5-(dimethylamino)methylfurfuryl alcohol was fed through a conduit 3 to a reactor 1 maintained at a temperature of 20° to 30° C. Aqueous hydrochloric acid solution of 5-(dimethylamino)-methylfurfuryl alcohol hydrochloride thus obtained was continuously fed to a reactor 5 through a conduit 4. Under maintaining a temperature of the reactor at 50° to 60° C., 13.3 kg/hr of an aqueous 75 wt% cysteamine hydrochloride solution was continuously fed to the reactor 5 through a conduit 6. Further, a reaction product was continuously discharged from the reactor 5 through a conduit 7. Residence time at the reactor 1 was 10 minutes and the residence time at the reactor was 30 minutes.

The reaction product discharged from the reactor 5 was analyzed by gas chromatography to find that reaction yield of 2-[[[5-(dimethylamino)methyl-2-furanyl]-methylthio]-ethene amine was 89 mol% to 5-(dimethylamino)methyl furfuryl alcohol.

What is claimed is:

1. A method for the production of 2-[[[5-(dimethylamino)methyl-2-furanyl]methyl]thio]-ethane amine represented by the formula II:

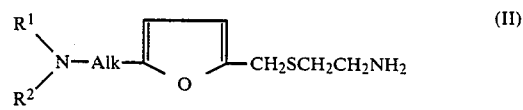

wherein $R^1$ and $R^2$ independently stand for an alkyl group of 1 to 4 carbon atoms and Alk stands for an alkylene group of 1 to 4 carbon atoms, by the reaction of 5-(dialkylamino)alkylfurfuryl alcohol represented by the formula I:

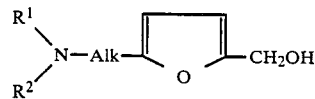

wherein $R^1$, $R^2$ and Alk have the same mean ing as defined above, with cysteamine or cysteamine hydrochloride in the presence of free excess concentrated aqueous hydrogen chloride at a temperature of 30° to 80° C. for from about 15 to about 180 minutes.

2. A method according to claim 1, wherein $R^1$ and $R^2$ independently stand for an alkyl group of 1 to 2 carbon atoms and Alk stands for alkylene group of 1 to 2 carbon atoms.

3. A method according to claim 1, wherein the total amount of hydrochloric acid is 3 to 6 mols per mol of 5-(dialkylamino)alkylfurfuryl alcohol.

4. A method according to claim 1, wherein the amount of cysteamine or hydrochloride thereof is in the range of 0.5 to 3 mols per mol of 5-(dialkylamino)alkylfurfuryl alcohol.

5. A method according to claim 1, wherein the amount of free hydrogen chloride is in the range of 1 to 5 mols per mol 5-(dialkylamino)alkylfurfuryl alcohol.

6. A method according to claim 1, wherein the reaction temperature is in the range of 40° to 70° C.

7. A method according to claim 1, wherein $R^1$ and $R^2$ are each methyl group and Alk is methylene group.

8. A method according to claim 1, wherein hydrochloric acid solution of 5-(dialkylamino)alkylfurfuryl alcohol hydrochloride and cysteamine or cysteamine hydrochloride are continuously fed to a reactor, the mixture is subjected to a reaction and then the reaction product is continuously discharged from said reactor.

9. A method according to claim 8, wherein said hydrochloric acid solution of 5-(dialkylamino)alkylfurfuryl alcohol hydrochloride is previously produced by feeding hydrochloric acid and 5-(dialkylamino)alkylfurfuryl alcohol into an another reactor maintained at a temperature of 0° to 80° C.

* * * * *